US009386788B2

(12) United States Patent
Ahn

(10) Patent No.: US 9,386,788 B2
(45) Date of Patent: Jul. 12, 2016

(54) ISOMALTOOLIGOSACCHARIDE COMPOSITIONS CONTAINING ISOMALTULOSE, METHODS FOR PREPARING THE SAME AND USES THEREOF

(71) Applicant: Sang-Wook Ahn, Incheon-Si (KR)

(72) Inventor: Sang-Wook Ahn, Incheon-Si (KR)

(73) Assignee: Corn Products Development, Inc., Sao Paulo (BR)

( * ) Notice: Subject to any disclaimer, the term of this patent is extended or adjusted under 35 U.S.C. 154(b) by 0 days.

(21) Appl. No.: 14/282,128

(22) Filed: May 20, 2014

(65) Prior Publication Data

US 2016/0081382 A1    Mar. 24, 2016

(30) Foreign Application Priority Data

May 20, 2013  (KR) .................. 10-2013-0056533

(51) Int. Cl.
```
C08B 37/00      (2006.01)
A23L 1/236      (2006.01)
A23L 1/09       (2006.01)
C12P 19/14      (2006.01)
C12P 19/24      (2006.01)
C12P 19/22      (2006.01)
C13K 7/00       (2006.01)
C13K 11/00      (2006.01)
C13K 13/00      (2006.01)
```
(52) U.S. Cl.
CPC ............. *A23L 1/2365* (2013.01); *A23L 1/095* (2013.01); *C12P 19/14* (2013.01); *C12P 19/22* (2013.01); *C12P 19/24* (2013.01); *C13K 7/00* (2013.01); *C13K 11/00* (2013.01); *C13K 13/00* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 4,376,824 | A * | 3/1983 | Hurst ................. | F16L 58/02 435/94 |
| 4,501,814 | A * | 2/1985 | Schoenrock ........... | C12P 19/24 435/94 |
| 4,898,820 | A | 2/1990 | Hitoshio | |
| 6,025,168 | A * | 2/2000 | Vercauteren .......... | C13K 13/00 435/101 |
| 8,637,103 | B2 | 1/2014 | Kwon | |
| 9,057,087 | B2 * | 6/2015 | Prata ................. | C12P 19/02 |
| 2009/0305360 | A1 * | 12/2009 | Breneman ............. | C12P 7/00 435/96 |

FOREIGN PATENT DOCUMENTS

| | | | | | |
|---|---|---|---|---|---|
| BR | WO 2012068047 | A2 * | 5/2012 | ............ | C12P 19/02 |
| GB | 1456262 | A * | 11/1976 | ............ | C13K 11/00 |
| GB | 2097400 | A * | 11/1982 | ............ | C12P 19/24 |

OTHER PUBLICATIONS

Daohai Zhang, Isomaltulose Synthase (Pall) of *Klebsiella* sp. LX3, The Journal of Biological Chemistry, Sep. 12, 2003, pp. 35428-35434, vol. 278, No. 37, The American Society for Biochemistry and Molecular Biology, Inc., USA.

* cited by examiner

*Primary Examiner* — Melvin C Mayes
*Assistant Examiner* — Stefanie Cohen
(74) *Attorney, Agent, or Firm* — John Daniel Wood; Karen G. Kaiser

(57) ABSTRACT

The present application relates to novel isomaltooligosaccharide (IMO) compositions containing isomaltulose, methods for preparing the same and uses thereof. Specifically, the IMO compositions according to the present application containing isomaltulose, which is a sugar component not contained in currently available isomaltooligosaccharide products, have a quality of sweetness and degree of sweetness differentiated from the existing isomaltooligosaccharide products and thus can be used as sweeteners for more various applications.

20 Claims, 5 Drawing Sheets

ISOMALTOOLIGOSACCHARIDE COMPOSITIONS CONTAINING ISOMALTULOSE, METHODS FOR PREPARING THE SAME AND USES THEREOF

FIELD OF THE INVENTION

The present application relates to novel isomaltooligosaccharide (IMO) compositions containing isomaltulose, methods for preparing the same and uses thereof. Specifically, the IMO compositions according to the present application containing isomaltulose, which is a sugar component not contained in currently available isomaltooligosaccharide products, have a quality of sweetness and degree of sweetness differentiated from the existing isomaltooligosaccharide products and thus can be used as sweeteners for more various applications.

BACKGROUND OF THE INVENTION

Currently available isomaltooligosaccharide (IMO) products contain isomaltose, panose, isomaltotriose, isomaltotetraose, isomaltopentaose, isomaltohexaose, etc., but do not contain isomaltulose.

Isomaltooligosaccharides are oligosaccharides that exhibit excellent physiological activity in the human body, e.g., they help intestinal regulation (causes the proliferation of beneficial enteric bacteria) and aid in the improvement of constipation, etc. Isomaltooligosaccharides are mainly used to impart health functionality to dairy products and are functional saccharide substances that dominate the oligosaccharide markets in Japan and Korea.

Currently, isomaltooligosaccharides are produced by using starch as a raw material through liquefaction and saccharification, followed by purification including filtration, decolorization, ion-exchange, evaporation and the like. The conventional processes of preparing IMO comprise the saccharification of an liquefaction solution obtained by liquefying starch, where the saccharification may be performed by carrying out maltose saccharification ($1^{st}$ saccharification) and isomaltooligosaccharide saccharification ($2^{nd}$ saccharification) separately and sequentially as shown in FIG. 1 or by carrying out maltose saccharification and isomaltooligosaccharide saccharification simultaneously as shown in FIG. 2.

In addition, alpha-amylase may be used as a liquefaction enzyme, beta-amylase and pullulanase are used as a maltose saccharification enzyme, and transglucosidase may be used as an isomaltooligosaccharide saccharification enzyme.

Further, isomaltulose, which is also called palatinose, is a disaccharide in which dextrose and fructose are linked by an alpha-1,6 bond and is a sweetener ingredient that is non-cariogenic and slowly digested and absorbed.

DESCRIPTION OF THE INVENTION

Problems to be Solved by the Invention

It is an object of the present application to provide novel isomaltulose-containing isomaltooligosaccharide (IMO) compositions that have a quality of sweetness and degree of sweetness differentiated from the existing IMO products and thus can be used as a sweetener for a wide variety of applications.

It is another object of the present application to provide methods for preparing the above novel isomaltulose-containing IMO compositions.

It is yet another object of the present application to provide sweeteners comprising the above isomaltulose-containing IMO compositions.

It is still another object of the present application to provide food stuff comprising the above isomaltulose-containing IMO compositions.

Means to Solve Problems

In order to achieve the above objects, the present application provides isomaltooligosaccharide compositions comprising from 29 to 40% by weight of fructose, from 29 to 36% by weight of dextrose, from 15 to 18% by weight of isomaltooligosaccharide, from 2 to 9% by weight of isomaltulose, from 1 to 10% by weight of maltose, and from 0 to 12% by weight of maltotriose and higher polysaccharides, based on the total weight of solids.

In addition, the present application provides isomaltooligosaccharide compositions containing isomaltulose obtained by methods comprising the steps of:
a) liquefying a starch slurry by contacting with a liquefaction enzyme to obtain a liquefaction solution;
b) saccharifying the obtained liquefaction solution to dextrose by contacting with a first saccharification enzyme;
c) isomerizing the obtained dextrose-containing product to fructose by contacting with an isomerization enzyme; and
d) saccharifying an isomaltooligosaccharide saccharification solution to isomaltooligosaccharide by contacting with a mixture of a second saccharification enzyme and a third saccharification enzyme, where the isomaltooligosaccharide saccharification solution is obtained by adding the liquefaction solution obtained in step a) to the fructose-containing product obtained in step c).

Further, the present application provides isomaltooligosaccharide compositions containing isomaltulose obtained by methods comprising saccharifying a slurry of at least one raw material for saccharification selected from fructose and sucrose to isomaltooligosaccharide by contacting with a first saccharification enzyme.

In addition, the present application provides methods for preparing isomaltooligosaccharide compositions containing isomaltulose, comprising the steps of:
a) liquefying a starch slurry by contacting with a liquefaction enzyme to obtain a liquefaction solution;
b) saccharifying the obtained liquefaction solution to dextrose by contacting with a first saccharification enzyme;
c) isomerizing the obtained dextrose-containing product to fructose by contacting with an isomerization enzyme; and
d) saccharifying an isomaltooligosaccharide saccharification solution to isomaltooligosaccharide by contacting with a mixture of a second saccharification enzyme and a third saccharification enzyme, wherein the isomaltooligosaccharide saccharification solution is obtained by adding the liquefaction solution obtained in step a) to the fructose-containing product obtained in step c).

Further, the present application provides methods for preparing isomaltooligosaccharide compositions containing isomaltulose, comprising saccharifying a slurry of at least one raw material for saccharification selected from fructose and sucrose to isomaltooligosaccharide by contacting with a first saccharification enzyme.

In addition, the present application provides sweeteners comprising the above isomaltulose-containing IMO composition.

In addition, the present application provides food stuff comprising the above isomaltulose-containing IMO composition.

Effects of the Invention

The novel isomaltulose-containing IMO compositions according to the present application, unlike the existing IMO products where dextrose makes up the majority of the monosaccharide, contain fructose as well as dextrose, and isomaltulose which is a disaccharide, and thus have an improved quality of sweetness and degree of sweetness, such that they can be used as sweeteners for a wide variety of applications.

DETAILED DESCRIPTION FOR PRACTICING THE INVENTION

Figure 1:
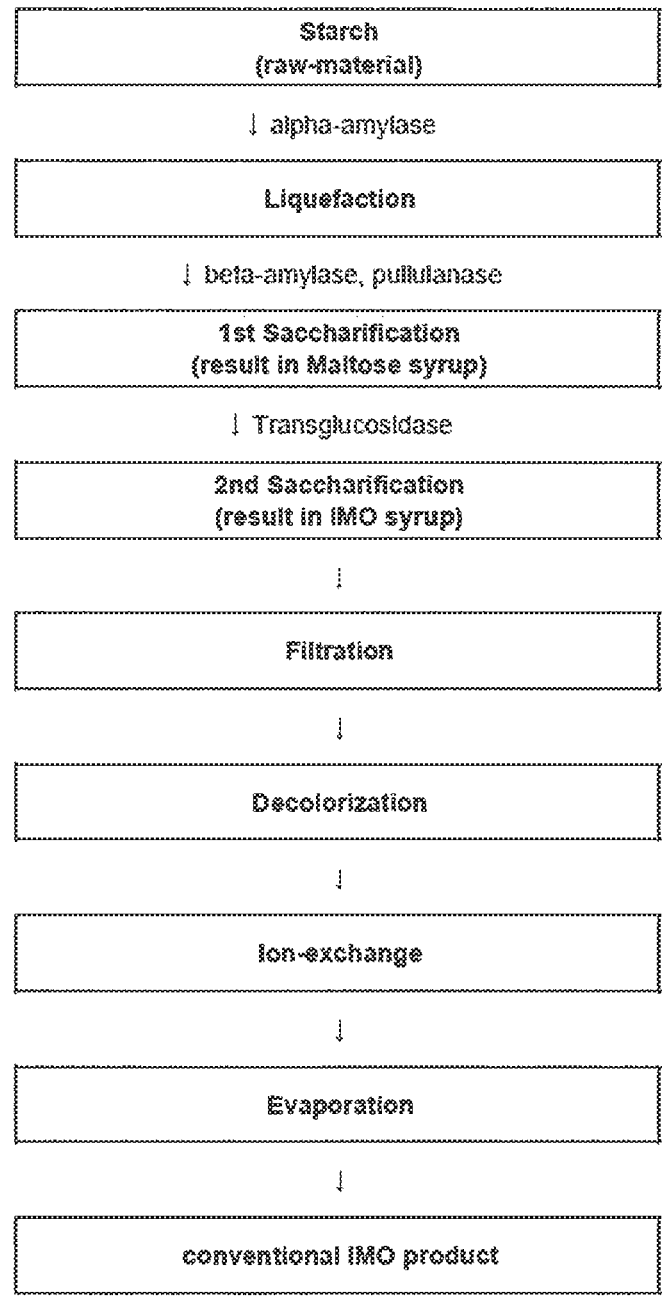
FIGS. 1 and 2 schematically show exemplary processes for preparing conventional IMO products.
Figure 2:
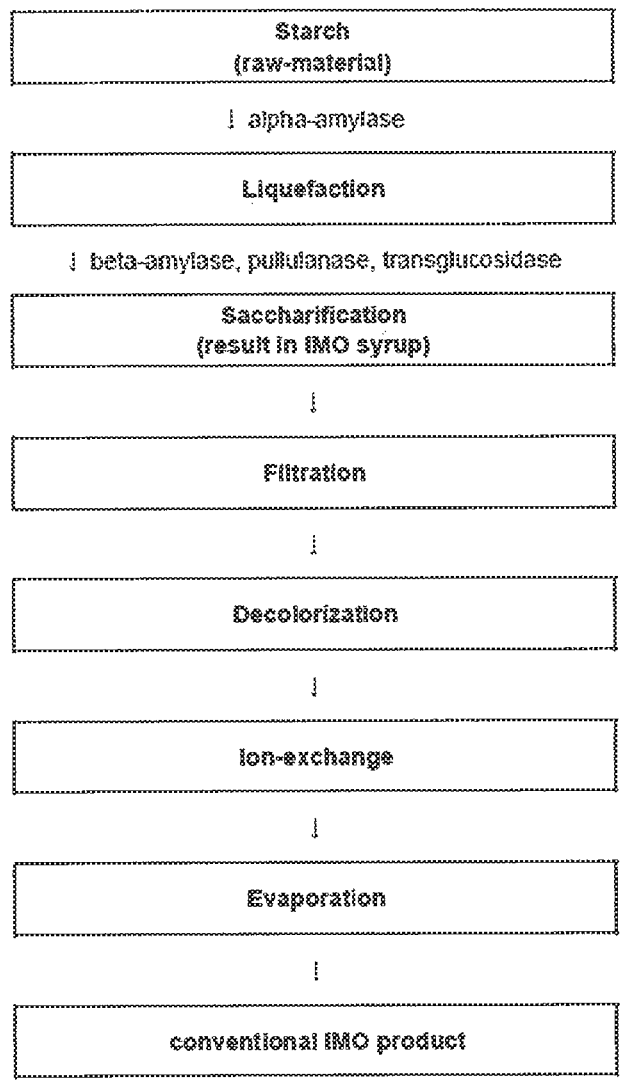

The novel isomaltulose-containing IMO compositions according to the present application comprise from 29 to 40 DB % of fructose, from 29 to 36 DB % of dextrose, from 15 to 18 DB % of isomaltooligosaccharide, from 2 to 9 DB % of isomaltulose, from 1 to 10 DB % of maltose, and from 0 to 12 DB % of maltotriose and higher polysaccharides (e.g., maltotetraose, maltopentaose, maltohexaose, etc.), where the DB % represents the percentage on a dry basis.

The isomaltulose-containing IMO compositions according to the present application have sugar compositions differentiated from those of the existing IMO compositions as shown in Table 1 below.

TABLE 1

| Sugar Compositions | Conventional IMOs <DB %> | IMOs of Present Application <DB %> |
| --- | --- | --- |
| fructose | 0 | 29-40 |
| dextrose | 18-22 | 29-36 |
| isomaltooligosaccharide | 50-55 | 15-18 |
| isomaltulose | 0 | 2-9 |
| maltose | 12-18 | 1-10 |
| maltotriose and higher polysaccharides | 10-15 | 0-12 |

The novel isomaltulose-containing IMOs of the present application contain fructose and isomaltulose which are not contained in the conventional IMO products and thus have a quality of sweetness and degree of sweetness differentiated from the existing IMOs, and thus can be used as sweeteners for a wide variety of applications.

The isomaltulose-containing IMO compositions of the present application can be prepared by, for example, the following two methods.

First, an isomaltulose-containing IMO composition can be prepared by a method comprising the steps of: a) liquefying a starch slurry by contacting with a liquefaction enzyme to obtain a liquefaction solution; b) saccharifying the obtained liquefaction solution to dextrose by contacting with a first saccharification enzyme; c) isomerizing the obtained dextrose-containing product to fructose by contacting with an isomerization enzyme; and d) saccharifying an isomaltooligosaccharide saccharification solution to isomaltooligosaccharide by contacting with a mixture of a second saccharification enzyme and a third saccharification enzyme, where the isomaltooligosaccharide saccharification solution is obtained by adding the liquefaction solution obtained in step a) to the fructose-containing product obtained in step c).

This method may additionally include, for example, purification steps including filtration, decolorization, ion-exchange, etc., as described in Korean Laid-Open Patent Publication No. 2012-0019391, following at least one step selected from the group consisting of the above liquefaction step a), dextrose saccharification step b), isomerization step c) and isomaltooligosaccharide saccharification step d), and the above purification step may include an evaporation step for removing moisture to enhance the storability of the product.

In the present application, starch may be any substance consisting of polysaccharide carbohydrates. Examples of starch that may be used include, but are not limited to, corn starch, rice starch, wheat starch, potato starch, sweet potato starch, barley starch, sorghum starch, and mixtures thereof.

The starch slurry may be a starch suspension in which starch is dispersed in an aqueous solvent such as water, at concentrations of 10 to 50% (w/w), specifically 5 to 40% (w/w), more specifically 30 to 40% (w/w), or most specifically 34 to 38% (w/w) based on solids.

As used herein, the term "liquefaction enzyme" means one of many alpha-amylases or other amylases. Liquefaction enzymes affect the fluidity or viscosity of starch, i.e., starch fluidization. In the method of the present application, the liquefaction enzyme may be, for example, alpha-amylase; the first saccharification enzyme may be, for example, glucoamylase; and the isomerization enzyme may be, for example, dextrose-isomerase. As used herein, the term "saccharification enzyme" means one or more enzymes that are capable of hydrolyzing polysaccharides and/or oligosaccharides, for example, alpha-1,4-glucosidic bonds of starch. As used herein, the term "saccharification" means the acid- or enzymic-hydrolysis of starch or liquefied starch or maltodextrins or maltooligosaccharides that ultimately results in the production of D-glucose, maltose, small maltooligosaccharides, or any mixtures thereof.

In the present application, the process for obtaining a liquid fructose using starch as a raw material via the steps of liquefaction, dextrose saccharification, and isomerization, i.e., the above steps a), b), and c), can be carried out similar to the process for preparing the existing liquid fructose product (HFCS-55, Ingredion Korea) commercially available in the market (see [Fred W. Schenck and Ronald E. Hdbeda, *Starch Hydrolysis Products*, 1992], [Harry M. Pancoast and W. Ray Junk, *Handbook of Sugars*, 1980]. [Lyn O'Brien Nabors, *Alternative Sweeteners*, 2001], etc.).

In the present application, the isomaltooligosaccharide saccharification step d) can be carried out by contacting an isomaltooligosaccharide saccharification solution with a mixture of a second saccharification enzyme and a third saccharification enzyme, where the isomaltooligosaccharide saccharification solution can be obtained by adding the liquefaction solution obtained in step a) to the fructose-containing product obtained in step c).

For the fructose-containing products that are used in the above step d), the crude fructose product obtained in step c) or the high purity fructose concentrates that are obtained by carrying out the purification process including filtration, decolorization, ion-exchange and evaporation, etc. or mixtures thereof may be used. The fructose-containing products specifically contain at least 42% (w/w) of fructose.

In addition, in the above step d), the amount of the liquefaction solution added in the fructose-containing product may be in the range of 30 to 60% (w/w) based on the total weight of the isomaltooligosaccharide saccharification solution.

Further, in the above step d), the concentration of raw material for isomaltooligosaccharide saccharification in the isomaltooligosaccharide saccharification solution may be in the range of from 10 to 70% (w/w), specifically from 20 to 60% (w/w), more specifically from 30 to 50% (w/w), or most specifically from 35 to 40% (w/w).

In step d) of the present application, the second saccharification enzyme may be, for example, fungal-alpha-amylase or beta-amylase, and the amount of the second saccharification enzyme added may be in the range of 0.001 to 5.0% (w/w) based on the total weight of solids in the isomaltooligosaccharide saccharification solution. Additionally, the second saccharification enzyme may further include from 0.001 to 3.0% (w/w) of pullulanase based on the total weight of solids in the isomaltooligosaccharide saccharification solution.

In addition, the third saccharification enzyme may be, for example, transglucosidase, and the amount of the third saccharification enzyme added may be in the range of 0.001 to 5.0% (w/w) based on the total weight of solids in the isomaltooligosaccharide saccharification solution.

Further, the mixture of the second saccharification enzyme and third saccharification enzyme may be added in the range of 0.001 to 5.0% (w/w) based on the total weight of solids in the isomaltooligosaccharide saccharification solution.

The isomaltooligosaccharide saccharification step d) may be carried out at a temperature in the range of 40 to 70° C. and at a pH in the range of 4.5 to 6.5 for 10 to 120 hours.

According to the above methods of the present application, isomaltulose-containing IMO compositions which contain from 1 to 20% by weight of isomaltulose based on the total weight of solids and from 10 to 30% by weight of isomaltooligosaccharide based on the total weight of hydrates can be prepared.

In addition, the second method of the present application for preparing isomaltulose-containing IMO compositions comprises saccharifying a solution of at least one raw material for saccharification selected from fructose and sucrose to isomaltooligosaccharide by contacting with a first saccharification enzyme.

In this method, the fructose that is used as a raw material for saccharification may be a liquid fructose having a fructose content of equal to or greater than 35% on a dry basis and the sucrose may be raw sugar before purification, sugar after purification (e.g., white sugar, brown sugar, and black sugar), or mixtures thereof.

In addition, the solution of the above raw material for saccharification may be an aqueous solution obtained by dissolving the raw material for saccharification in an aqueous solvent such as water at a concentration of 30 to 90% (w/w).

In this method, the above raw material for saccharification may be a mixture of fructose and dextrose or taffies, a mixture of sucrose and dextrose or taffies, or mixtures thereof, besides fructose and sucrose.

In this method, the first saccharification enzyme may be a glucoamylase that is a dextrose saccharification enzyme explained above.

The amount of the first saccharification enzyme added may be in the range of 0.1 to 10% (w/w) based on the total weight of solids in the saccharification solution.

This saccharification may be carried out at a temperature in the range of 50 to 80° C. and at a pH in the range of 4.0 to 6.0 for 12 to 120 hours.

By such saccharification, IMO compositions containing from 1 to 20% by weight of isomaltulose based on the total weight of solids and from 10 to 30% by weight of isomaltooligosaccharide based on the total weight of hydrates can be prepared.

EMBODIMENTS

The following embodiments are presented to further illustrate and explain the present invention and should not be taken as limiting in any regard.

1. An isomaltooligosaccharide composition comprising from about 27% to about 42% by weight of fructose, from about 27% to about 38% by weight of dextrose, from about 10% to about 30% by weight of isomaltooligosaccharide, from about 1% to about 20% by weight of isomaltulose, from about 1% to about 12% by weight of maltose, from about 0% to 14% by weight of maltotriose and higher polysaccharides, based on the total weight of solids.

2. The isomaltooligosaccharide composition of embodiment 1 comprising from about 29% to about 40% by weight of fructose, from about 29 to about 36% by weight of dextrose, from about 15 to about 18% by weight of isomaltooligosaccharide, from about 2% to about 9% by weight of isomaltulose, from about 1% to about 10% by weight of maltose, from about 0% to 12% by weight of maltotriose and higher polysaccharides, based on the total weight of solids.

3. The isomaltooligosaccharide composition of embodiment 2 comprising from about 29% to about 33% by weight of fructose, from about 29% to about 33% by weight of dextrose, from about 15% to about 18% by weight of isomaltooligosaccharide, from about 2% to about 5% by weight of isomaltulose, from about 6% to about 10% by weight of maltose, from about 1% to 12% by weight of maltotriose and higher polysaccharides, based on the total weight of solids.

4. The isomaltooligosaccharide composition of embodiment 2 comprising from about 36% to about 40% by weight of fructose, from about 32% to about 36% by weight of dextrose, from about 15% to about 18% by weight of isomaltooligosaccharide, from about 5% to about 9% by weight of isomaltulose, from about 1% to about 3% by weight of maltose, from about 0% to 2% by weight of maltotriose and higher polysaccharides, based on the total weight of solids.

5. A method for preparing the isomaltooligosaccharide composition of embodiment 1 containing isomaltulose, comprising the steps of:
   a) liquefying a starch slurry by contacting with a liquefaction enzyme to obtain a liquefaction solution;
   b) saccharifying the obtained liquefaction solution to dextrose by contacting with a first saccharification enzyme;
   c) isomerizing the obtained dextrose-containing product to fructose by contacting with an isomerization enzyme; and
   d) saccharifying an isomaltooligosaccharide saccharification solution to isomaltooligosaccharide by contacting with a mixture of a second saccharification enzyme and a third saccharification enzyme, where the isomaltooligosaccharide saccharification solution is obtained by adding the liquefaction solution obtained in step a) to the fructose-containing product obtained in step c).

6. The method according to embodiment 5, wherein a purification step is additionally carried out after at least one step selected from the group consisting of step a), step b), step c), and step d).

7. The method according to embodiment 6, wherein the purification step includes filtration, decolorization, ion-exchange, and evaporation.

8. The method according to embodiment 5, wherein the starch is at least one selected from the group consisting of corn starch, rice starch, wheat starch, potato starch, sweet potato starch, barley starch and sorghum starch.

9. The method according to embodiment 5, wherein the starch slurry is obtained by suspending a starch in water at a concentration from about 10% to about 50% by weight based on solids.

10. The method according to embodiment 5, wherein the liquefaction enzyme is alpha-amylase.

11. The method according to embodiment 5, wherein the first saccharification enzyme is glucoamylase.

12. The method according to embodiment 5, wherein the isomerization enzyme is dextrose-isomerase.

13. The method according to embodiment 5, wherein the fructose-containing product contains at least 42% (w/w) of fructose based on solids.

14. The method according to embodiment 5, wherein, in step d), the amount of the liquefaction solution added to the fructose-containing product is in the range from about 30% to about 60% (w/w) based on the total weight of the isomaltooligosaccharide saccharification solution.

15. The method according to embodiment 5, wherein the concentration of raw material for isomaltooligosaccharide saccharification in the isomaltooligosaccharide saccharification solution is from about 10% to about 70% (w/w).

16. The method according to embodiment 5, wherein the second saccharification enzyme is a fungal alpha-amylase or beta-amylase.

17. The method according to embodiment 5, wherein the amount of the second saccharification enzyme added is in the range from about 0.001% to about 5% (w/w) based on the total weight of solids in the isomaltooligosaccharide saccharification solution.

18. The method according to embodiment 16 or 17, wherein the second saccharification enzyme further comprises pullulanase in an amount from about 0.001% to about 3% (w/w) based on the total weight of solids in the isomaltooligosaccharide saccharification solution.

19. The method according to embodiment 5, wherein the third saccharification enzyme is transglucosidase.

20. The method according to embodiment 19, wherein the amount of the third saccharification enzyme added is in the range of 0.001 to 5% (w/w) based on the total weight of solids in the isomaltooligosaccharide saccharification solution.

21. The method according to embodiment 5, wherein the mixture of the second saccharification enzyme and the third saccharification enzyme is added at a concentration from about 0.001% to about 5% (w/w) based on the total weight of solids in the isomaltooligosaccharide saccharification solution.

22. The method according to embodiment 5, wherein the isomaltooligosaccharide saccharification step d) is carried out at a temperature in the range from about 40° C. to about 70° C. and at a pH in the range from about 4.5 to about 6.5 for about 10 hours to about 120 hours.

23. The method according to embodiment 5, wherein the obtained IMO composition contains from about 1% to about 20% by weight of isomaltulose based on the total weight of solids and from about 10% to about 30% by weight of isomaltooligosaccharide based on the hydrates.

24. A method for preparing the isomaltooligosaccharide composition containing isomaltulose of embodiment 1, comprising saccharifying a solution of at least one raw material for saccharification selected from fructose and sucrose to isomaltooligosaccharide by contacting with a first saccharification enzyme.

25. The method according to embodiment 24, wherein the fructose is liquid fructose.

26. The method according to embodiment 24, wherein the sucrose is selected from raw sugar before purification, sugar after purification, or any mixtures thereof.

27. The method according to embodiment 24, wherein the solution of raw material for saccharification is obtained by dissolving the raw material for saccharification in water at a concentration from about 30% to about 90% (w/w).

28. The method according to embodiment 24, wherein the raw material for saccharification comprises a mixture of fructose and dextrose or taffies, a mixture of sucrose and dextrose or taffies, or mixtures thereof.

29. The method according to embodiment 24, wherein the first saccharification enzyme is glucoamylase.

30. The method according to embodiment 24, wherein the first saccharification enzyme is added at a concentration from about 0.1% to about 10% (w/w) based on the total weight of solids in the saccharification solution.

31. The method according to embodiment 24, wherein the saccharification is carried out in a temperature range from about 50° to 80° C. and at a pH in the range from about 4 to about 6 for about 12 hours to about 120 hours.

32. The method according to embodiment 24, wherein the obtained IMO composition contains from 1 to 20% by weight of isomaltulose based on the total weight of solids and from 10 to 30% by weight of isomaltooligosaccharide based on the hydrates.

33. The isomaltooligosaccharide composition containing isomaltulose obtained by the method according to embodiment 5.

34. The isomaltooligosaccharide composition containing isomaltulose obtained by the method according to embodiment 24.

35. A sweetener comprising an isomaltooligosaccharide composition according to any one of embodiments 1, 33, and 34.

36. Food stuff comprising the isomaltooligosaccharide composition according to any one of embodiments 1, 33, and 34.

Embodiments

The following embodiments are presented to further illustrate and explain the present invention and should not be taken as limiting in any regard.

1. An isomaltooligosaccharide composition comprising from about 27% to about 42% by weight of fructose, from about 27% to about 38% by weight of dextrose, from about 10% to about 30% by weight of isomaltooligosaccharide, from about 1% to about 20% by weight of isomaltulose, from about 1% to about 12% by weight of maltose, from about 0% to 14% by weight of maltotriose and higher polysaccharides, based on the total weight of solids.

2. The isomaltooligosaccharide composition of embodiment 1 comprising from about 29% to about 40% by weight of fructose, from about 29 to about 36% by weight of dextrose, from about 15 to about 18% by weight of isomaltooligosaccharide, from about 2% to about 9% by weight of isomaltulose, from about 1% to about 10% by weight of maltose, from about 0% to 12% by weight of maltotriose and higher polysaccharides, based on the total weight of solids.

3. The isomaltooligosaccharide composition of embodiment 2 comprising from about 29% to about 33% by weight of fructose, from about 29% to about 33% by weight of dextrose, from about 15% to about 18% by weight of isomaltooligosaccharide, from about 2% to about 5% by weight of isomaltulose, from about 6% to about 10% by weight of maltose, from about 1% to 12% by weight of maltotriose and higher polysaccharides, based on the total weight of solids.

4. The isomaltooligosaccharide composition of embodiment 2 comprising from about 36% to about 40% by weight of fructose, from about 32% to about 36% by weight of dextrose, from about 15% to about 18% by weight of isomaltooligosaccharide, from about 5% to about 9% by weight of isomaltulose, from about 1% to about 3% by weight of maltose, from about 0% to 2% by weight of maltotriose and higher polysaccharides, based on the total weight of solids.

5. A method for preparing the isomaltooligosaccharide composition of embodiment 1 containing isomaltulose, comprising the steps of:
    a) liquefying a starch slurry by contacting with a liquefaction enzyme to obtain a liquefaction solution;
    b) saccharifying the obtained liquefaction solution to dextrose by contacting with a first saccharification enzyme;
    c) isomerizing the obtained dextrose-containing product to fructose by contacting with an isomerization enzyme; and
    d) saccharifying an isomaltooligosaccharide saccharification solution to isomaltooligosaccharide by contacting with a mixture of a second saccharification enzyme and a third saccharification enzyme, where the isomaltooligosaccharide saccharification solution is obtained by adding the liquefaction solution obtained in step a) to the fructose-containing product obtained in step c).

6. The method according to embodiment 5, wherein a purification step is additionally carried out after at least one step selected from the group consisting of step a), step b), step c), and step d).

7. The method according to embodiment 6, wherein the purification step includes filtration, decolorization, ion-exchange, and evaporation.

8. The method according to embodiment 5, wherein the starch is at least one selected from the group consisting of corn starch, rice starch, wheat starch, potato starch, sweet potato starch, barley starch and sorghum starch.

9. The method according to embodiment 5, wherein the starch slurry is obtained by suspending a starch in water at a concentration from about 10% to about 50% by weight based on solids.

10. The method according to embodiment 5, wherein the liquefaction enzyme is alpha-amylase.

11. The method according to embodiment 5, wherein the first saccharification enzyme is glucoamylase.

12. The method according to embodiment 5, wherein the isomerization enzyme is dextrose-isomerase.

13. The method according to embodiment 5, wherein the fructose-containing product contains at least 42% (w/w) of fructose based on solids.

14. The method according to embodiment 5, wherein, in step d), the amount of the liquefaction solution added to the fructose-containing product is in the range from about 30% to about 60% (w/w) based on the total weight of the isomaltooligosaccharide saccharification solution.

15. The method according to embodiment 5, wherein the concentration of raw material for isomaltooligosaccharide saccharification in the isomaltooligosaccharide saccharification solution is from about 10% to about 70% (w/w).

16. The method according to embodiment 5, wherein the second saccharification enzyme is a fungal alpha-amylase or beta-amylase.

17. The method according to embodiment 5, wherein the amount of the second saccharification enzyme added is in the range from about 0.001% to about 5% (w/w) based on the total weight of solids in the isomaltooligosaccharide saccharification solution.

18. The method according to embodiment 16 or 17, wherein the second saccharification enzyme further comprises pullulanase in an amount from about 0.001% to about 3% (w/w) based on the total weight of solids in the isomaltooligosaccharide saccharification solution.

19. The method according to embodiment 5, wherein the third saccharification enzyme is transglucosidase.

20. The method according to embodiment 19, wherein the amount of the third saccharification enzyme added is in the range of 0.001 to 5% (w/w) based on the total weight of solids in the isomaltooligosaccharide saccharification solution.

21. The method according to embodiment 5, wherein the mixture of the second saccharification enzyme and the third saccharification enzyme is added at a concentration from about 0.001% to about 5% (w/w) based on the total weight of solids in the isomaltooligosaccharide saccharification solution.

22. The method according to embodiment 5, wherein the isomaltooligosaccharide saccharification step d) is carried out at a temperature in the range from about 40° C. to about 70° C. and at a pH in the range from about 4.5 to about 6.5 for about 10 hours to about 120 hours.

23. The method according to embodiment 5, wherein the obtained IMO composition contains from about 1% to about 20% by weight of isomaltulose based on the total weight of solids and from about 10% to about 30% by weight of isomaltooligosaccharide based on the hydrates.

24. A method for preparing the isomaltooligosaccharide composition containing isomaltulose of embodiment 1, comprising saccharifying a solution of at least one raw material for saccharification selected from fructose and sucrose to isomaltooligosaccharide by contacting with a first saccharification enzyme.

25. The method according to embodiment 24, wherein the fructose is liquid fructose.

26. The method according to embodiment 24, wherein the sucrose is selected from raw sugar before purification, sugar after purification, or any mixtures thereof.

27. The method according to embodiment 24, wherein the solution of raw material for saccharification is obtained by dissolving the raw material for saccharification in water at a concentration from about 30% to about 90% (w/w).

28. The method according to embodiment 24, wherein the raw material for saccharification comprises a mixture of fructose and dextrose or taffies, a mixture of sucrose and dextrose or taffies, or mixtures thereof.

29. The method according to embodiment 24, wherein the first saccharification enzyme is glucoamylase.

30. The method according to embodiment 24, wherein the first saccharification enzyme is added at a concentration from about 0.1% to about 10% (w/w) based on the total weight of solids in the saccharification solution.

31. The method according to embodiment 24, wherein the saccharification is carried out in a temperature range from about 50° to 80° C. and at a pH in the range from about 4 to about 6 for about 12 hours to about 120 hours.

32. The method according to embodiment 24, wherein the obtained IMO composition contains from 1 to 20% by weight of isomaltulose based on the total weight of solids and from 10 to 30% by weight of isomaltooligosaccharide based on the hydrates.

33. The isomaltooligosaccharide composition containing isomaltulose obtained by the method according to embodiment 5.

34. The isomaltooligosaccharide composition containing isomaltulose obtained by the method according to embodiment 24.

35. A sweetener comprising an isomaltooligosaccharide composition according to any one of embodiments 1, 33, or 34.

36. Food stuff comprising the isomaltooligosaccharide composition according to any one of embodiments 1, 33, or 34.

EXAMPLES

The present application is further described and illustrated according to the examples provided below. However, it should be noted that the following examples are presented only for illustrative purposes and are not intended to limit the scope of the present application.

Example 1

Figure 3:
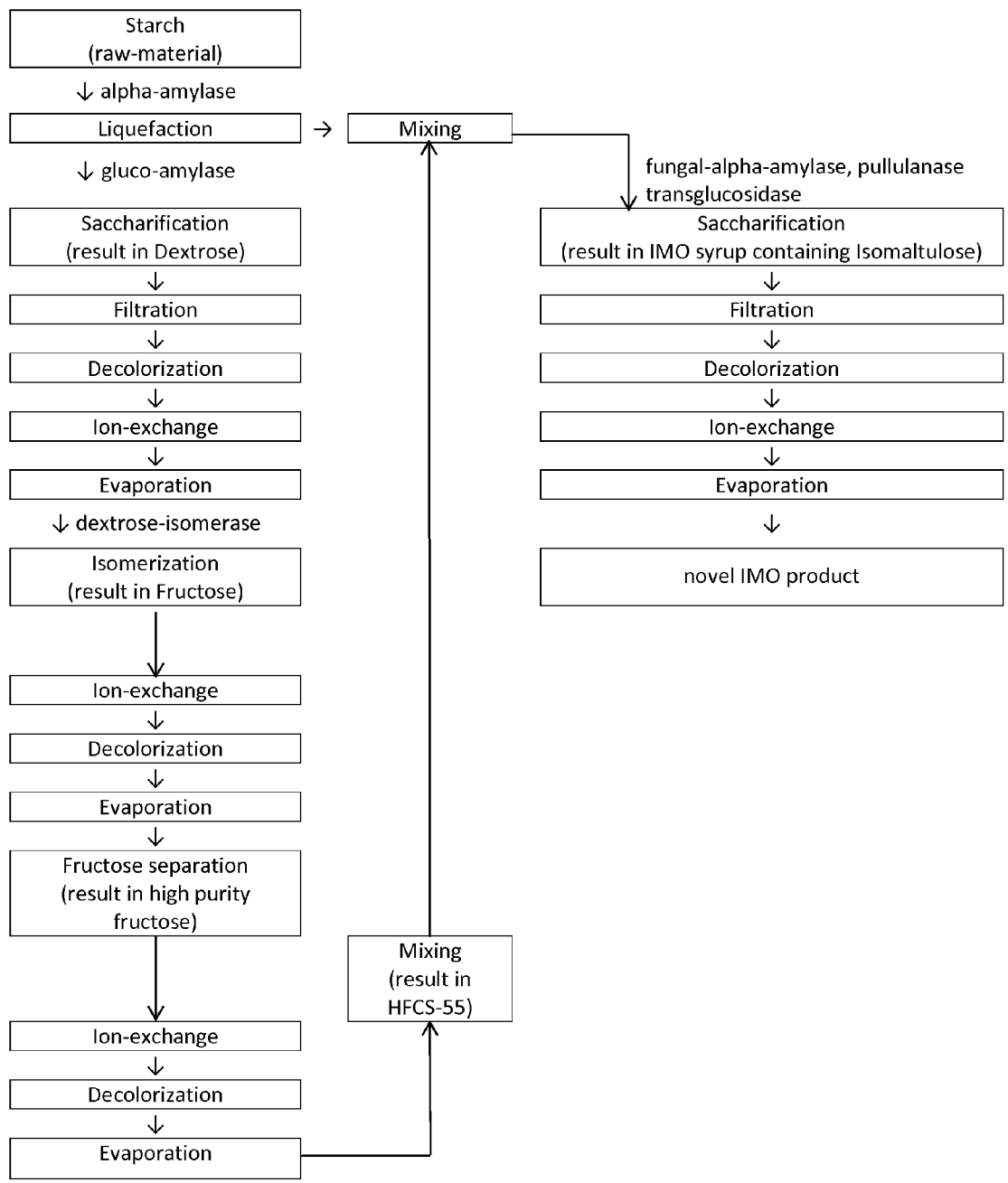
FIG. 3 schematically shows a process for preparing the IMO composition according to Example 1.

As shown in FIG. 3, isomaltulose-containing IMO compositions of the present application were prepared by carrying out a process using starch as a raw material and various types of enzymes (alpha-amylase, glucoamylase, dextrose-isomerase, fungal-alpha-amylase, pullulanase, transglucosidase, etc.):

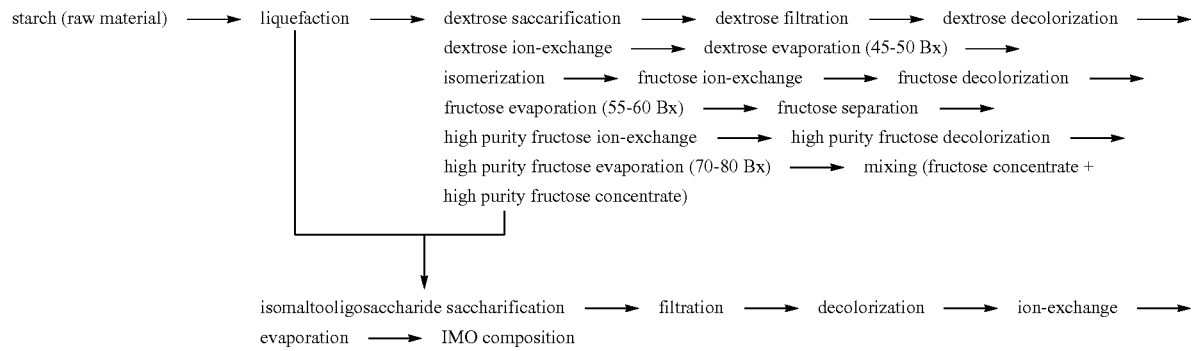

Specifically, 2,600 g of corn starch and 6,000 g of water were added to a vessel to prepare starch slurry. A liquefaction enzyme, alpha-amylase (Liquozyme Supra 2.2×, Novozymes Korea), was added to the starch slurry in an amount of 0.04 to 0.05% (w/w) based on the total weight of solids in the starch slurry at a pH of 5.5 to 6.0, followed by a reaction for 5 to 30 minutes at a temperature of 100 to 110° C. to obtain a liquefaction solution with a dextrose equivalent (DE) of 10 to 14. Subsequently, the obtained liquefaction solution was subject to the dextrose saccharification step. Specifically, glucoamylase (Dextrozyme 2.0×, Novozymes Korea) was added in an amount of 0.05 to 0.08% (w/w) based on the total weight of solids in the obtained liquefaction solution at a pH of 4.2 to 4.5, followed by a reaction for 40 to 48 hours at a temperature of 55 to 60° C. The obtained saccharification solution was subject to filtration to remove the unreacted materials, followed by decolorization by passing the solution through a carbon column filled with granular active carbon at a temperature of 70 to 75° C. for 30 minutes to 2 hours. Subsequently, ionic components were removed from the solution using a cation exchange resin (PK218, Samyang) and an anion exchange resin (WA30, Samyang) with a flow rate of 50 to 150 L/min at 40 to 50° C. Next, the obtained solution was evaporated by means of an evaporator to 45 to 50 Bx to obtain a dextrose concentrate.

Then, the obtained dextrose concentrate was passed through a column filled with an isomerization enzyme (Gensweet, Okjun Biotech) at a temperature of 60 to 65° C. and at a pH of 7.7 to 8.0 to obtain an isomerization solution having a fructose content of 40 to 45% (w/w) based on solids, and ionic substances were removed therefrom using a cation exchange resin (PK218, Samyang) and an anion exchange resin (WA30, Samyang). To the ion-purified solution was added powdered active carbon, and the solution was subject to decolorization at a temperature of 70 to 75° C. for 30 minutes to 1 hour, followed by filtration using 5A and 5C filter papers and evaporation to obtain a fructose concentrate of 55 to 60 Bx. Subsequently, the obtained fructose concentrate was passed through a column filled with a resin for a separator (Dowex Monosphere 99 Ca/320, Dow) at 60 to 62° C. to obtain a high purity fructose solution having a fructose content of equal to or greater than 85% (w/w) based on solids. The obtained high purity fructose solution was subject to ion purification using a cation exchange resin (PK218, Samyang) and an anion exchange resin (WA30, Samyang), decolorization using granular active carbon, and evaporation to obtain a high purity fructose concentrate of 70 to 80 Bx.

Next, the high purity fructose concentrate was mixed with the above fructose concentrate (55~60 Bx) so as to have a fructose content of 55-57% (w/w) based on solids, followed by addition of water to obtain a sugar solution of 35 to 38 Bx. The sugar solution was then mixed with approximately 40% by weight, based on the total weight of the sugar solution, of the liquefaction solution (Bx: 35 to 38, DE: 10 to 14) to obtain raw material for isomaltooligosaccharide saccharification.

To the obtained raw material for isomaltooligosaccharide saccharification, 0.03 to 0.06% (w/w) of fungal-alpha-amylase (Clarase L, Okjun Biotech), 0.011 to 0.014% (w/w) of pullulanase (Optimax L1000, Okjun Biotech), and 0.024 to 0.027% (w/w) of transglucosidase (Transglucosidase L "Amano", Sein Corporation), based on the total weight of solids of the raw material for isomaltooligosaccharide saccharification, were added and followed by reaction at a temperature of 55 to 60° C. and at a pH 5.2 to 5.6 for 40 to 48 hours to obtain an isomaltooligosaccharide composition containing isomaltulose. The obtained solution was subject to filtration to remove unreacted materials and passed through a column filled with granular active carbon at a temperature of 70 to 75° C. for 30 minutes to 2 hours. Ionic components such as sodium and calcium ions were removed from the solution using a cation exchange resin (PK218, Samyang) and an anion exchange resin (WA30, Samyang), and the solution was evaporated by means of an evaporator to obtain an isomaltulose-containing isomaltooligosaccharide composition of 75 to 77 Bx.

The term "Bx" used herein indicates the solid concentration in a solution at a given temperature, which is measured using a Brix-meter. Accordingly, Bx is a measurement of sugar solubilized in a solution. The Brix-meter measures the grams of sugar present in 100 g of solution. For example, 1.0 Bx represents 10 mg/ml of sugar in the solution.

The sugar compositions of the IMO compositions obtained from Example 1 and the conventional IMO product (IMO-R1, Ingredion Korea) were analyzed by HPLC (High Performance Liquid Chromatography), and the results are shown in Table 2 below.

TABLE 2

| Sugar Composition | Conventional IMOs (DB %) | IMOs of Example 1 (DB %) |
| --- | --- | --- |
| fructose | 0 | 29~33 |
| dextrose | 18~22 | 29~33 |
| isomaltooligosaccharide | 50~55 | 15~18 |
| isomaltulose | 0 | 2~5 |
| maltose | 12~18 | 6~10 |
| maltotriose and higher polysaccharides | 10~15 | 1~12 |

Example 2

Figure 4:
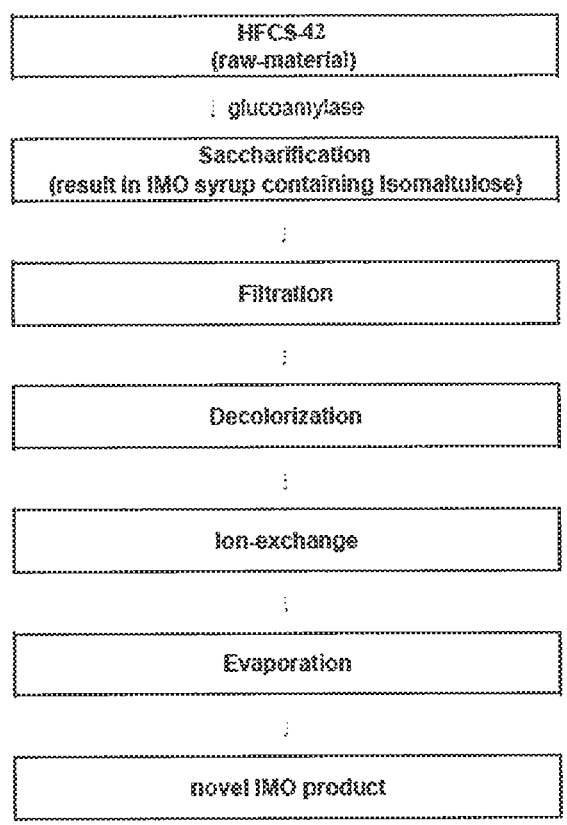
FIG. 4 schematically shows a process for preparing the IMO composition according to Example 2.

As shown in FIG. 4, the IMO compositions of the present application were prepared by carrying out a process using liquid fructose as a raw material and a glucoamylase enzyme:

liquid fructose (raw material)→saccharification (enzymatic reaction)→filtration→decoloization→ion-exchange→evaporation→IMO composition Specifically, an isomaltooligosaccharide saccharification solution with Bx of 70 to 73 was obtained by adding water to a liquid fructose (HFCS-42, Ingredion Korea) having a fructose content of 42 to 45% (w/w) based on solids and Bx of 75 to 77. To the solution was added a dextrose saccharification enzyme, glucoamylase (AMG, Novozymes Korea), in an amount of 2.0 to 2.5% (w/w) based on the total weight of solids in the saccharification solution at a temperature of 65 to 70° C. and a pH of 4.3 to 4.7, followed by a reaction for 90 to 96 hours. The obtained solution was subject to filtration using diatomite to remove the unreacted materials, decolorization by passing through a column filled with granular active carbon at a temperature of 70 to 75° C., ion purification using a cation exchange resin (PK218, Samyang) and an anion exchange resin (WA30, Samyang), and evaporation to remove moisture to obtain an isomaltulose-containing isomaltooligosaccharide composition with Bx of 75 to 77.

The sugar compositions of the IMO compositions obtained from Example 2 and the conventional IMO products (IMO-R1, Ingredion Korea) were analyzed by HPLC, and the results are shown in Table 3 below.

TABLE 3

| Sugar Composition | Conventional IMOs (DB %) | IMOs of Example 2 (DB %) |
| --- | --- | --- |
| fructose | 0 | 36~40 |
| dextrose | 18~22 | 32~36 |
| isomaltooligosaccharide | 50~55 | 15~18 |
| isomaltulose | 0 | 5~9 |
| maltose | 12~18 | 1~3 |
| maltotriose and higher polysaccharides | 10~15 | 0~2 |

Experimental Example 1

Sensory Evaluation of the IMO Composition According to Example 1

Figure 5:
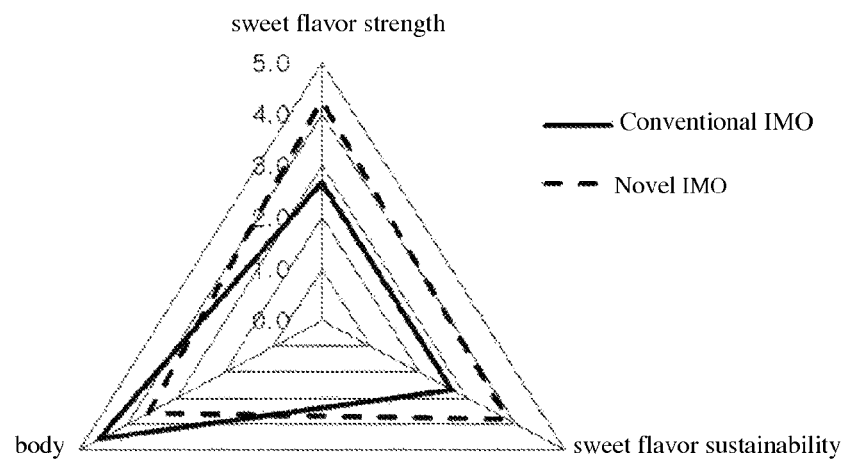
FIG. 5 is a graph comparing the sensory evaluations of the IMO composition according to Example 1 and a conventional IMO product.

The sweetness strength, sweetness sustainability, and body of the isomaltooligosaccharide composition prepared by Example 1 (novel IMO) and the conventional isomaltooligosaccharide product (conventional IMO, IMO-R1, Ingredion Korea) were compared by a sensory test, and the results are shown in FIG. 5.

Specifically, the conventional IMO and novel IMO samples were each prepared into a 10% solution based on solids. After being kept cool at 4° C. for 8 to 16 hours, the solutions were subject to sensory tests in the sensory testing laboratory at room temperature. In the sensory test, a 5-scale test was used to evaluate each property (sweetness strength, sweetness sustainability, body) and the panel trained on the sweetness of sweeteners was composed of 12 employees of Ingredion Korea aged between 25 and 50.

As shown in FIG. 5, the novel IMO composition according to Example 1 of the present application showed remarkable differences in the three sensory properties, i.e., it had a higher sweetness strength, longer sweetness sustainability, and lighter body in comparison to the conventional IMOs. It could also be ascertained from the sensory test results that the novel IMO exhibited sweetness more close to sugar than the conventional IMOs.

Experimental Example 2

Sensory Evaluation of the IMO Composition According to Example 2

Figure 6:
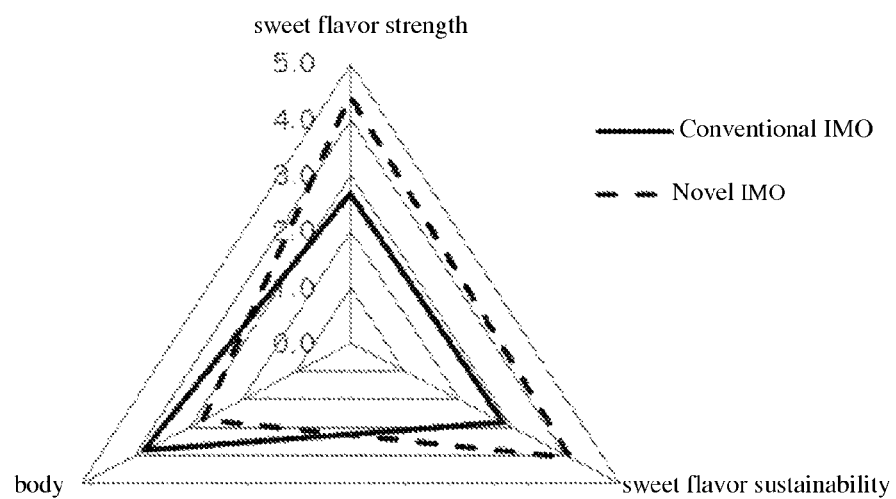
FIG. 6 is a graph comparing the sensory evaluations of the IMO composition according to Example 2 and a conventional IMO product.

The sensory properties, i.e., sweetness strength, sweetness sustainability and body of the isomaltooligosaccharide composition (novel IMO) prepared by Example 2 were evaluated in a similar manner to that described in Experimental Example 1, and the results are shown in FIG. 6.

As shown in FIG. 6, the novel IMO composition according to Example 2 of the present application also showed remarkable differences in the three sensory properties, i.e., it had a higher sweetness strength, longer sweetness sustainability, and lighter body in comparison to the conventional IMOs. It could also be ascertained from the sensory test results that the novel IMO exhibited a sweetness more close to sugar than the conventional IMOs.

What is claimed:

1. An isomaltooligosaccharide composition comprising from 27% to 42% by weight of fructose, from 27% to 38% by weight of dextrose, from 10% to 30% by weight of isomaltooligosaccharide, from 1% to 20% by weight of isomaltulose, from 1% to 12% by weight of maltose, from 0% to 14% by weight of maltotriose and higher polysaccharides, based on the total weight of solids.

2. The isomaltooligosaccharide composition of claim 1 comprising from 29% to 40% by weight of fructose, from 29 to 36% by weight of dextrose, from 15 to 18% by weight of isomaltooligosaccharide, from 2% to 9% by weight of isomaltulose, from 1% to 10% by weight of maltose, from 0% to 12% by weight of maltotriose and higher polysaccharides, based on the total weight of solids.

3. The isomaltooligosaccharide composition of claim 2 comprising from 29% to 33% by weight of fructose, from 29% to 33% by weight of dextrose, from 15% to 18% by weight of isomaltooligosaccharide, from 2% to 5% by weight of isomaltulose, from 6% to 10% by weight of maltose, from 1% to 12% by weight of maltotriose and higher polysaccharides, based on the total weight of solids.

4. The isomaltooligosaccharide composition of claim 2 comprising from 36% to 40% by weight of fructose, from 32% to 36% by weight of dextrose, from 15% to 18% by weight of isomaltooligosaccharide, from 5% to 9% by weight of isomaltulose, from 1% to 3% by weight of maltose, from 0% to 2% by weight of maltotriose and higher polysaccharides, based on the total weight of solids.

5. A method for preparing the isomaltooligosaccharide composition of claim 1 containing isomaltulose, comprising the steps of:
   a) liquefying a starch slurry by contacting with a liquefaction enzyme to obtain a liquefaction solution;
   b) saccharifying the obtained liquefaction solution to dextrose by contacting with a first saccharification enzyme;
   c) isomerizing the obtained dextrose-containing product to fructose by contacting with an isomerization enzyme; and
   d) saccharifying an isomaltooligosaccharide saccharification solution to isomaltooligosaccharide by contacting with a mixture of a second saccharification enzyme and a third saccharification enzyme, where the isomaltooligosaccharide saccharification solution is obtained by adding the liquefaction solution obtained in step a) to the fructose-containing product obtained in step c).

6. The method according to claim 5, wherein a purification step, which includes filtration, decolorization, ion-exchange, and evaporation, is additionally carried out after at least one step selected from the group consisting of step a), step b), step c), and step d).

7. The method according to claim 5, wherein the starch is at least one selected from the group consisting of corn starch, rice starch, wheat starch, potato starch, sweet potato starch, barley starch and sorghum starch.

8. The method according to claim 5, wherein the starch slurry is obtained by suspending a starch in water at a concentration from 10% to 50% by weight based on solids.

9. The method according to claim 5, wherein the liquefaction enzyme is alpha-amylase.

10. The method according to claim 5, wherein the first saccharification enzyme is glucoamylase.

11. The method according to claim 5, wherein the isomerization enzyme is dextrose-isomerase.

12. The method according to claim 5, wherein, in step d), the amount of the liquefaction solution added to the fructose-containing product is in the range from 30% to 60% (w/w) based on the total weight of the isomaltooligosaccharide saccharification solution.

13. The method according to claim 5, wherein the concentration of raw material for isomaltooligosaccharide saccharification in the isomaltooligosaccharide saccharification solution is from 10% to 70% (w/w).

14. The method according to claim 5, wherein the second saccharification enzyme is a fungal alpha-amylase or beta-amylase.

15. The method according to claim 14, wherein the second saccharification enzyme further comprises pullulanase in an amount from 0.001% to 3% (w/w) based on the total weight of solids in the isomaltooligosaccharide saccharification solution.

16. The method according to claim 5, wherein the third saccharification enzyme is transglucosidase.

17. The method according to claim 16, wherein the amount of the third saccharification enzyme added is in the range of 0.001 to 5% (w/w) based on the total weight of solids in the isomaltooligosaccharide saccharification solution.

18. The method according to claim 5, wherein the isomaltooligosaccharide saccharification step d) is carried out at a temperature in the range from 40° C. to 70° C. and at a pH in the range from 4.5 to 6.5 for 10 hours to 120 hours.

19. A sweetener comprising an isomaltooligosaccharide composition according to claim 1.

20. Food stuff comprising the isomaltooligosaccharide composition according to claim 1.

* * * * *